United States Patent [19]

Shiono

[11] Patent Number: 5,154,690

[45] Date of Patent: Oct. 13, 1992

[54] SUPPORTER

[75] Inventor: Katuaki Shiono, Hatogaya, Japan

[73] Assignee: Tokyo Eizai Laboratory Company, Ltd., Tokyo, Japan

[21] Appl. No.: 664,634

[22] Filed: Mar. 4, 1991

[30] Foreign Application Priority Data

Mar. 5, 1990 [JP] Japan .................. 2-54265

[51] Int. Cl.5 ............................. A61H 5/00
[52] U.S. Cl. .......................... 602/5; 602/61; 602/63; 602/6; 602/21; 602/23; 602/26; 602/27
[58] Field of Search ............... 128/77, 157, 165, 166, 128/80 R, 80 C, 80 H; 2/16, 22, 44; 602/5, 6, 20, 21, 23, 26, 27, 61–65

[56] References Cited

U.S. PATENT DOCUMENTS

| | | | |
|---|---|---|---|
| 4,622,908 | 11/1986 | Tranberg | 128/80 C |
| 4,765,318 | 8/1988 | Tranberg | 128/80 C |
| 4,832,010 | 5/1989 | Lerman | 128/165 |
| 4,961,418 | 10/1990 | McLaurin-Smith | 128/77 |

Primary Examiner—Richard J. Apley
Assistant Examiner—Linda C. M. Dvorak
Attorney, Agent, or Firm—Haverstock, Garrett & Roberts

[57] ABSTRACT

A supporter for mounting on a limb in position to cover an affected body portion to predeterminedly constrain and limit movement thereof comprising a tubular stretchable elastic material forming a main body and having adhered to at least one portion of the main body a reinforcing member comprising an interlining laminated to a surface member which acts to restrict the elongation of said interlining, wherein the reinforcing member has a modulus of elasticity capable of restricting movement of an affected body part within a defined motion area.

13 Claims, 5 Drawing Sheets

5,154,690

SUPPORTER

The present invention relates to a supporter which is used for fixing, supporting, pressing, protecting, and the like by covering a portion of the human body, and in particular the present invention relates to a medical supporter used for preventing and curing of orthopedic troubles in bone, muscle, tendon, and so on and to a supporter used for protecting a portion of the human body from injury during sports activities and from a relapse of an injury.

BACKGROUND OF THE INVENTION

Supporters for fixing, supporting, pressing, protecting, and retaining warmth by covering a portion of the human body are well known. For example, there are supporters for use on a joint such as the shoulder, elbow, hand, hip, knee, and the ankle, and supporters for use on limbs such as the forearm, upper arm, thigh, and the shank, for medical and sports purposes. That is, there are various kinds of supporters based on the body part on which the supporter is used and the nature of the trouble. Such supporters act to fix, support, press, protect, and retain warmth in a particular part of the human body by combining an elastic member with a non-elastic member or an auxiliary belt.

DETAILED DESCRIPTION OF THE PREFERRED EMBODIMENTS

Figure 6:
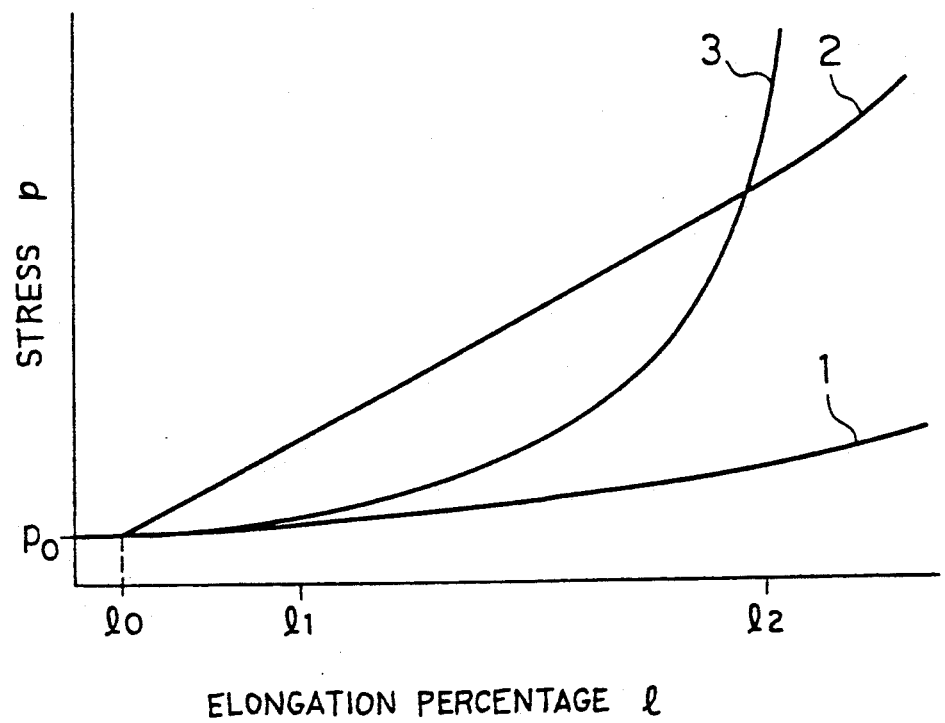
FIG. 6 is a graphical illustration showing the relationship between the elongation and the stress characteristics of the subject supporters.

The relationship between the elongation percentage and the stress for a typical conventional supporter is shown by a characteristic curve on the graph of FIG. 6. In the graph of FIG. 6, the abscissa shows the elongation percentage of the supporter designated by the letter 1 and the ordinate shows the stress on the affected body part designated by the letter p. The point $p_0$ on the ordinate shows the stress on the affected part needed to attach the supporter, which is a minimum stress needed to prevent the supporter from slipping down from its desired location on the affected body part and the point $l_0$ on the abscissa is the elongation percentage corresponding to the minimum stress $p_0$. The curve designated by the numeral 1 has a small slope between the elongation percentage and the stress, that is, the stress or resultant effects or pressure on the affected body portion increases gradually even though the elongation percentage increases more markedly. The stress shown by the curve 1 is small within a scope of activities of daily living represented by the range of elongation percentage $l_0$ to $l_1$ wherein it is easy to move the affected body part in the uses of everyday life. The stress increases proportionally within a motion area represented by the elongation percentage from $l_1$ to $l_2$, wherein, for instance, it is necessary to move the affected body part in an unusual activity. The stress increases proportionally even within a critical area or dangerous zone of elongation percentage of more than $l_2$, wherein there is a possibility of causing an injury or harm to the affected body part if the affected part is further moved. Since only a small stress is developed during the movement of the affected part in the scope of activities of daily living, a supporter providing the stress characteristics shown in curve 1 is desirable for wear during daily activities ($l_0$ to $l_1$) as such wear would not result in pain. However, since the stress to control the movement of the affected body part is still small when the movement of the affected part falls within the dangerous zone (beyond $l_2$), there is a possibility of an injury or harm to the affected part. Accordingly, use of a supporter having the characteristics of curve 1 would not prevent injury or harm to the affected part and there is a possibility that the supporter will slip down when the movement of the affected part is substantial and forceful.

Curve 2 has a larger slope than that of curve 1. Since in curve 2 the stress applied on the affected part in the dangerous zone (beyond $l_2$) is larger than that of curve 1, there is less possibility of applying an unusual force on the affected part. However, since the stress applied on the affected part in the scope of activities of daily living ($l_0$ to $l_1$) and the motion area ($l_1$ to $l_2$) are also relatively large for a supporter having the characteristics of curve 2, a greater pressure than is ordinarily needed in everyday life is applied to the affected part. Therefore, a supporter having the characteristics of curve 2 is not desirable because not only is the feeling of attachment excessive but also such a supporter can cause an interruption in blood circulation among other problems.

In curve 3 of FIG. 6, the stress remains low and does not change largely or substantially in the scope of activities of daily living ($l_0$ to $l_1$), but the stress increases exponentially in accordance with the increase of the elongation percentage in the motion area ($l_1$ to $l_2$), and the elongation does not further increase and does not enter into the dangerous zone (beyond $l_2$). If the supporter has such properties, there is no pain applied on the affected part because a very small amount of stress or pressure is applied on the affected part in everyday life, and the movement of the affected part is controlled by increasing the stress immediately when such movement becomes greater. The characteristic curve 3 is therefore ideal for a supporter for medical and sports uses. However, it is only possible to obtain the properties of the curves 1 and 2 from the known conventional supporters, a supporter having the property of curve 3 having not yet been obtained.

The object of the present invention is to provide an improved supporter for medical and sports use having the above mentioned ideal characteristic curve which fits or adheres and adapts to the condition of the affected body part and which is easily operable.

In order to achieve the above mentioned object, the present invention provides a supporter having a tubular shaped main body member of elastic material which fits on an affected body part with a reinforcing member attached or adhered to a portion of the main body member. The reinforcing member is formed by laminating an interlining layer having a greater modulus of elasticity than that of an elastic material forming the main body with a surface member for restricting the elongation of the interlining. The resulting laminated reinforcing member has a modulus of elasticity capable of restricting the movement of the affected body part within a particular motion area, motion area as that term is used meaning the scope of motion which is allowable in accordance with the condition of the affected part.

The position of the reinforcing member on the surface of the main body member is determined based on a so-called taping method. The taping method is used in the medical and sports fields, and is a method wherein the elongation of skin is restricted by an adhesive tape attached to the skin at a location corresponding to a muscle, ligament, joint, or other affected body part. The adhesive tape operates to support and protect the affected part by restricting the hyperextension of the affected part, the transmission of stress, and movement of the area of the affected part. For example, such taping method is used for coping with the stress caused by hard exercise and in sports activities, for coping with a secondary functional disorder after injury, for easing the condition of the secondary functional disorder, and for curing of general orthopedic trouble and assisting in rehabilitation after medical treatment. The position of the reinforcing member attached to the main body and pattern or shape thereof are determined so as to produce similar force by the reinforcing member as the force applied to the affected part by such taping method.

It is desirable that the elastic material forming the main body member of a supporter produce some stress or pressure on the affected part such that it remains in position thereon and does not slip down at the time of attaching. The elastic material should also be easy to fit to, and should conform with, the movement of skin, and it should be easy to attach and have a good air permeability. That is, a material having an elongation percentage characteristic equal to or more than 50%, and in particular having about 100% elongation percentage, is preferable for achieving attachment. A modulus of elasticity of about 0.12 to 0.48 kg/cm at the usual elongation percentage of 100% at the time of attaching is also desirable. An elastic knitted fabric or textile fabric using rubber thread or urethane thread can be used, and it can be formed in a tubular shape directly by a circular knitting machine or it can be formed in a tubular shape from a plain textile fabric by means of the added step of seaming such fabric into the tubular shape desired.

The reinforcing member is formed by laminating the interlining layer comprising a material having higher modulus of elasticity than that of the main body and a surface member comprising a material with a very small elasticity for restricting the elongation of the interlining to some degree. The interlining is desired to have a good air permeability, a strong backstretch or recovery, and a modulus of elasticity of about 0.18 to 0.72 kg/cm, which is 50% stronger or less elastic than the main body discussed above. For example, an elastic non-woven fabric such as a urethane non-woven fabric, i.e. trade name Espancione or the like, an elastic textile fabric such as a power net or the like, a film such as a urethane film having 75 to 100 um thickness, and a foam material such as urethane, chloroprene, or latex can be used as the interlining. As for the surface member, it is desirable to have some restriction against the elongation and also good air permeability. For example, although it depends on the affected part, the surface member can comprise woven fabric having from 30 to 150% elongation percentage which is less than that of the interlining, such as a fabric having a urethane thread having a low modulus of elasticity woven thereinto, or alternatively, a textile cloth such as a tricot fabric or a non-woven fabric can be used. As the best suitable materials, an elastic cloth of a plain fabric using a urethane thread of 40 denier in which the weight per unit area is 140 to 200 $g/m^2$ and the maximum elongation percentage is 50 to 100%, or a nylon tricot in which the weight per unit area is 120 $g/m^2$ and the maximum elongation percentage is 30 to 50%, can be used.

In order to laminate the interlining and the surface member, available adhesive agents such as in the form of a liquid type, a non-woven fabric type, and a film type can be used, which adhesive agents are used for adhesion of, for instance, chloroprene, polyurethane, acrylic, polyester, polyamide and styrene-isoprene-styrene fabrics. The liquid type adhesive agent is doped on the interlining and the surface member and the adhesive surfaces are laminated to each other to adhere both members by heating and drying under pressure. In case of the non-woven fabric type and the film type, such adhesive agents are inserted between the interlining and the surface member to adhere by using a heating roll. When the adhesive agent to be used is selected, it should be selected as having a high elastomeric content and should be one which is suitable for each material comprising the interlining and surface member, respectively. Some types of adhesive agents on the market which are suitable include, for example, adhesives such as identifiable by the tradenames Bond G-17 and 18 of KONISHI Co., Ltd., Evergrip of A.C.I. of Japan Ltd., Altecobond G-700 of Alpha Giken Co., Ltd., and Binezole R-550 and R-700 and Airpole R-1200 of Ipposha Oil Industries Co., Ltd.

The above mentioned adhesive agents also can be used for laminating the main body and the reinforcing member.

Importantly, in the above described supporter construction, the portion of the main body where the reinforcing member is not adhered is elastic according to the property of the elastic material alone, and the portion where the reinforcing member is adhered is elastic according to the property of the reinforcing member. When the supporter of the present invention is fitted or attached to a body part, it is easy to manipulate by stretching only the portion of the main body to which the reinforcing member is not attached. The change of the muscle and the ligament (hypertrophy, extension) is small in everyday life, and the elongation thereof falls within the scope or range which is possible to follow by elongation or other changing of the structure of the portion of the main body to which the reinforcing member is not attached to cope with the lower level of stress. When the motion becomes very large, the change of the muscle and the ligament also becomes large in accordance with such movement and the higher stress acts by adding the restraining action of the reinforcing member to the change of the main body to start the control of the movement of the affected body part. When the movement passes the limit, the surface member of the reinforcing member reaches the limit of elongation, and at this point the stress increases immediately to control the further movement of the affected part.

Alternative embodiments of the supporter according to the present invention will now be described.

EMBODIMENT 1: SUPPORTER FOR THE ANTERIOR CRUCIATE LIGAMENT

Figure 1A:
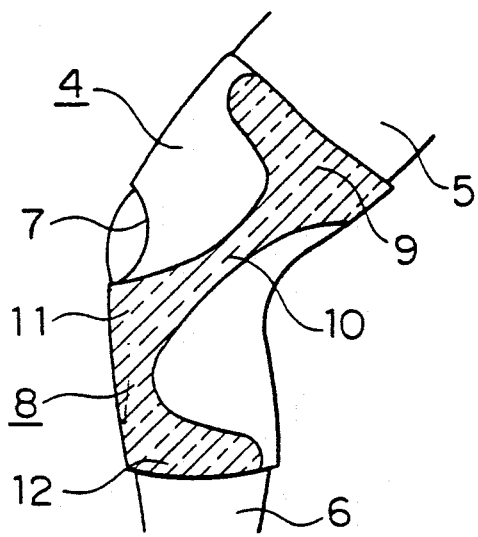
FIGS. 1a, 1b, and 1c are side, front, and rear views, respectively, showing the attached condition of one embodiment of the present supporter invention in position on a human knee.
Figure 1B:
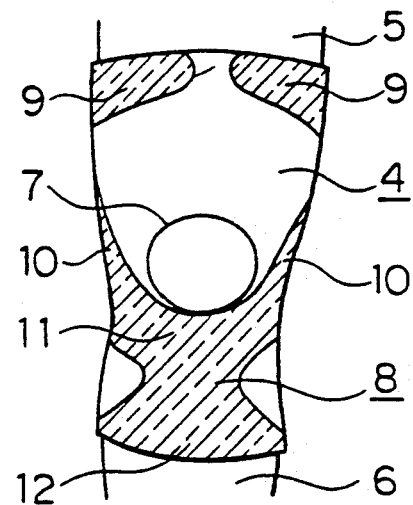
Figure 1C:
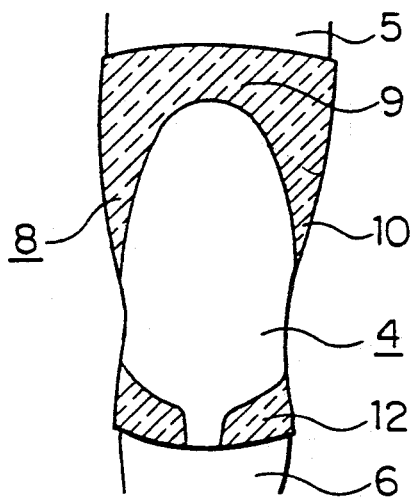
Figure 1D:
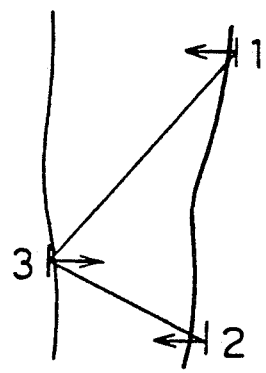
FIG. 1d is a side view of a human knee for illustrating the remedy principle used in the supporter construction shown in FIGS. 1a, 1b, and 1c.

This supporter is used for a knee problem such as a projection to forward of a shinbone or an instability in the front of the knee caused by damage or injury to the anterior cruciate ligament. As illustrated in FIG. 1d, the present supporter acts as follows; a tuberosity of the tibia 3 is pressed from forward against a back of thigh 1 and a back of leg 2 as fulcrums, and the knee joint is supported by three points so as not to exceed the movable area, thereby preventing and curing the injury or other trouble. FIGS. 1a, 1b, and 1c are side, front and rear views, respectively, showing the attached condition of the supporter for the anterior cruciate ligament according to the present invention. The reference numeral 4 is a tubular main body comprising an elastic material, and the main body 4 has a length and an inner diameter so as to cover the affected body part from a thigh 5 to the shank 6 and the main body 4 has an opening 7 having approximately the same size as that of a patella at approximately the center of the front portion thereof. The main body 4 is formed by a circular knitted fabric in which a urethane thread is knitted and has a tubular shape and the elasticity of the usual supporter. The modulus of elasticity is 0.08 kg/cm at 20% elongation percentage, 0.14 kg/cm at 50%, and 0.24 kg/cm at 100%, respectively. The reference numeral 8 is a reinforcing member formed by laminating an interlining and a surface member. For the interlining, a urethane non-woven textile cloth made by a spun bonding method having a weight per unit area of 180 g/m$^2$ is used, wherein the modulus of elasticity is 0.26 kg/cm at 20% elongation percentage, 0.45 kg/cm at 50, and 0.61 kg/cm at 100%, respectively. For the surface member, a nylon jersey material having a weight per unit area of 120 g/m$^2$ and a maximum elongation of 85%, and the modulus of elasticity of such laminated reinforcing member is 0.15 kg/cm at 20% elongation, 0.72 kg/cm at 50%, and at least 1 kg/cm at 100%, respectively. The reinforcing member 8 is unitarily formed on the surface of the main body 4 forming a pattern comprising a portion 9 for covering the upper side of the thigh region with 5 to 8 cm width except for 10 to 20% of the top of the front surface of the thigh region, a portion 10 for extending from both sides of the thigh region with 3 to 8 cm width to the lower side of the patella, a portion 11 in which the above two portions of 10 are combined at the lower side of the patella, and a portion 12 for covering the lower side of the leg except for 10 to 20% of the rear side of the lower shank thereof. The adhesion between the main body 4 and the reinforcing member 8 is achieved by a hot melt resin which is doped in the form of dots at a rate of 60 g/m$^2$ on the surface of the interlining and is adhered by hot pressing by means of an iron.

EMBODIMENT 2: SUPPORTER FOR A GONARTHROSIS DEGENERATIVE KNEE JOINT DISEASE

Figure 2A:
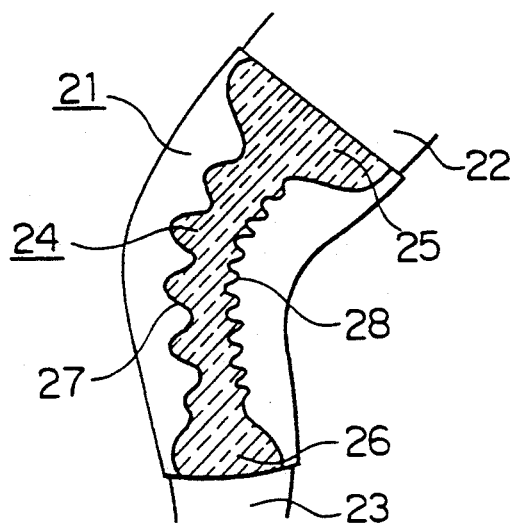
FIGS. 2a, 2b, and 2c are side, front, and rear views, respectively, showing the attached condition of a second embodiment of the present supporter invention in position on a human knee.
Figure 2B:
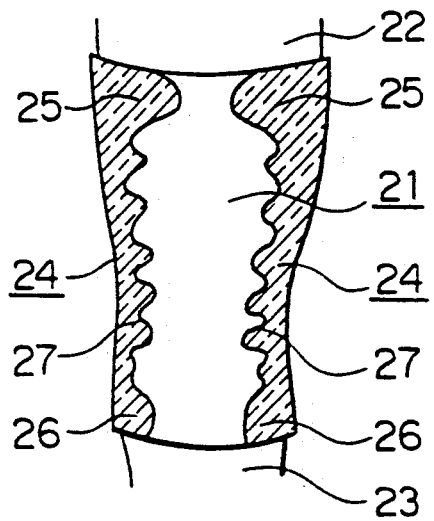
Figure 2C:
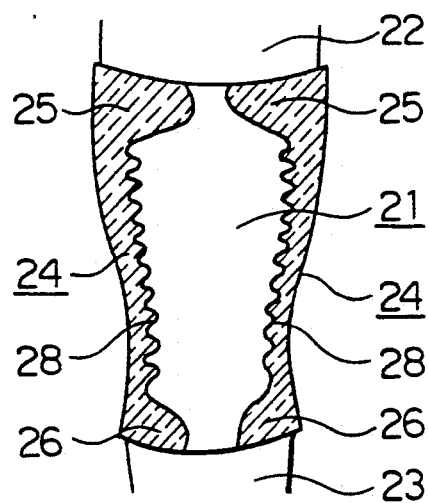

The gonarthrosis degenerative disease is an unstable knee problem in which the knee joint deforms to the right or left side and the knee joint sways. Such joint disease is prevented and cured by pressing the knee joint and the upper and lower region thereof (from lower side of the thigh region to upper side of the shank) uniformly at each side and by providing a support on both sides thereof. FIGS. 2a, 2b, and 2c are side, front, and rear views, respectively, showing the attached condition of the supporter for gonarthrosis degenerative disease according to the present invention.

The reference numeral 21 is a tubular main body comprising an elastic material and has a length and inner diameter to cover the affected body part from the thigh 22 to the shank 23. The main body 21 is formed by a circular knitted fabric in which a urethane thread is knitted and which has elasticity typical of a thermal supporter in which a pile is formed on the innerside of the main body. The modulus of elasticity of the main body 21 is relatively low, that is, about 0.07 kg/cm at 20% elongation percentage, 0.36 kg/cm at 50%, and 0.99 kg/cm at 100%, respectively. The surface member is a raschel knitted elastic cloth (such as elastic cloth, tradename Control of Asahi Chemical Co., Ltd.) having a weight per unit area of 220 g/m$^2$ and a 40% maximum elongation percentage. The modulus of elasticity of the reinforcing member 24 is 0.13 kg/cm at 20% elongation percentage, at least 1.0 kg/cm at 50%, and at least 1.0 kg/cm at 100%, respectively. The reinforcing member 24 covers the affected joint from the lower side 25 of the thigh region to the upper side 26 of the shank in the form of an I-shape on both sides of the main body 21. The reinforcing member 24 is unitarily formed on the surface of the main body 21 and has a pattern in which a large waveform is cut in the front side 27 and a smaller waveform is cut in the rear side 28. The main body 21 is unitarily formed with the reinforcing member 24 in that a thermoplastic adhesive is doped in the form of a mesh on the surface of the neoprene foam material of the reinforcing member and this is laminated on the surface of the main body, then the result is adhered by means of a hot press at 150° C. for 15 seconds.

EMBODIMENT 3: SUPPORTER FOR AN ANKLE JOINT

Figure 3A:
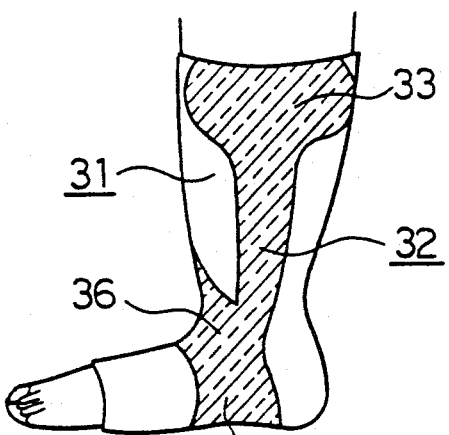
FIGS. 3a and 3b are side and front views, respectively, showing the attached condition of a third embodiment of the present invention in position on a human lower leg and ankle.
Figure 3B:
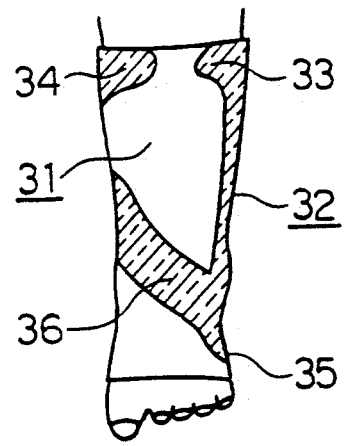

The injury to the ankle joint is most often a sprain. The supporter is used for fixing the ankle, in particular, in the case of where the ankle is abducted to cause trouble or injury in a low extensor muscle retinaculum. FIGS. 3a and 3b are side and front views showing the attached condition of the supporter for the ankle joint according to the present invention.

The reference numeral 31 is an open-toed sock type main body comprising an elastic material, and it is knitted to a thick cloth by a double raschel machine and has a modulus of elasticity of 0.06 kg/cm at 20% elongation percentage, 0.22 kg/cm at 50%, and 0.70 kg/cm at 100%, respectively. The reference numeral 32 refers to a reinforcing member formed by laminating an interlining and a surface member. The interlining is a urethane non-woven fabric having a weight per unit area of 120 g/m$^2$. The modulus of elasticity thereof is 0.06 kg/cm at 20% elongation percentage, 0.10 kg/cm at 50%, and 0.17 kg/cm at 100, respectively. The surface member is of a nylon tricot material having a weight per unit area of 130 g/m² and 35% maximum elongation, and the above nylon tricot is laminated by a chloeprene adhesive. The modulus of elasticity of the reinforcing member is 0.09 kg/cm at 20% elongation percentage, at least 1.0 kg/cm at 50%, and at least 1.0 kg/cm at 100%, respectively. The reinforcing member 32 is unitarily formed with the surface of the main body 31 and defines a pattern such that the reinforcing member 32 extends to the lower side from the upper ends 33 and 34 of both sides of the main body 31, reaching to the sole of the foot 35 in the form of a J-shape on the outer side. The reinforcing member 32 passes over the instep 36 on the inner side, thereby being combined with the outer reinforcing member. The main body 31 and the reinforcing member 32 are adhered to each other by the use of a thermoplastic adhesive which is doped on the surface of the urethane non-woven fabric of the reinforcing member in the form of a mesh, and this is laminated on the surface of the main body to adhere by means of a hot press at 150° C. for 15 minutes.

EMBODIMENT 4: SUPPORTER FOR A HUMEROUS OUTSIDE EPICONDYLE DISEASE (TENNIS ELBOW)

Figure 4A:
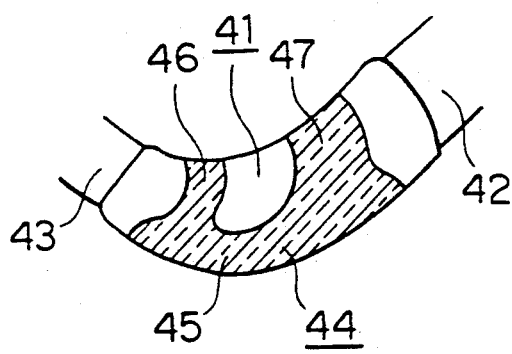
FIGS. 4a and 4b are opposite side views, respectively, showing the attached condition of a fourth embodiment of the present invention in position on a human elbow.
Figure 4B:
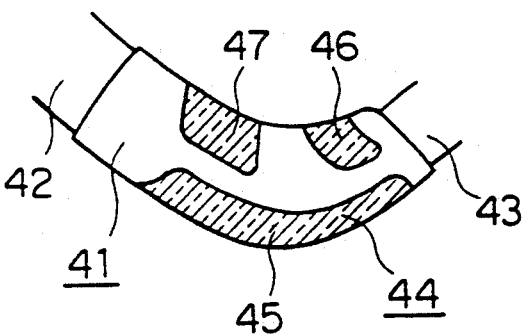

The outside epicondyle disease can be prevented and cured by applying pressure on the extensor muscles of the outside epicondyle at the portion of the forearm circumference flexed in the front of the eipcondyle to reduce force transmitted to the outside epicondyle. FIGS. 4a, and 4b are side views of the outer and the inner sides, respectively, of the attached condition of the supporter for humerous outside epicondyle disease according to the present invention.

The reference numeral 41 is a tubular main body comprising an elastic material and has a length and inner diameter for covering the affected body part from one portion of the upper arm 42 to one portion of the forearm 43. The tubular main body 41 is knitted by a circular knitting machine with 6 gages and a urethane thread of 1120 denier is inserted with the ratio of 4 pieces/cm as the elastic thread and the whole length is about 20 cm. The modulus of elasticity of the main body 41 is 0.08 kg/cm at 20% elongation percentage, 0.14 kg/cm at 50%, and 0.24 kg/cm at 100%, respectively. The reference numeral 44 is a reinforcing member formed by laminating an interlining and a surface member. As the interlining, a tricot fabric having an elastic thread comprising a urethane thread of 1120 denier inserted at a ratio of 8 pieces/cm and which is usually referred to as a power net, is used. The modulus of elasticity of the interlining is 0.2 kg/cm at 20% elongation percentage, 0.4 kg/cm at 50%, and 0.75 kg/cm at 100%, respectively. The surface member is a nylon raschel knitted fabric stretchable in two directions and having a weight per unit area of 160 g/m² and a 40% elongation percentage. The modulus of elasticity of the reinforcing member is 0.31 kg/cm at 20% elongation percentage, at least 1.0 kg/cm at 50%, and at least 1.0 kg/cm at 100%, respectively. The reinforcing member 44 is unitarily formed with the surface of the main body 41 and has a pattern covering a rear portion 45 from the upper arm to the forearm surface of the main body 41 which is approximately 4 to 7 cm in width, a rear portion 46 in a thumb side corresponding to 3 to 5 cm ahead of that portion of the forearm circumference flexed as shown in FIGS. 4a and 4b which is approximately 3 to 6 cm in width for about ¾ to 4/5 of whole circumference, and covering a portion 47 in the thumb side corresponding to 2 to 4 cm in the rear from the portion of the outside epicondyle as shown in FIGS. 4a and 4b which is approximately 3 to 6 cm in width for about ⅝ to ¾ of whole circumference. The main body 41 and the reinforcing member are adhered to each other by doping a nylon hot melt adhesive having a melting point of 105° with the ratio of 14 points/inch² and press heating it.

EMBODIMENT 5: SUPPORTER FOR POLLEX TENDOVAGINITIS

Figure 5:
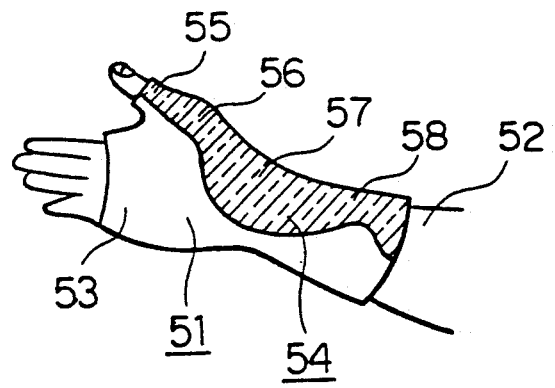
FIG. 5 is a side view showing the attached condition of a fifth embodiment of the present invention in position on a human elbow.

The supporter used for the pollex tendovaginitis has a structure for restricting the movement of the thumb and for keeping it quiet. FIG. 5 is a side view showing the attached condition of the supporter for the pollex tendovaginitis according to the present invention.

The reference numeral 51 is a tubular main body comprising an elastic material and which has a length and inner diameter for covering from the forearm 52 to the palm 53 of the hand. The tubular main body 51 is formed of a stretched plain weave fabric in which 24 non-elastic threads and 12 elastic threads of 840 denier urethane per inch for warp and 20 non-elastic threads per inch for woof are woven, and in which only the thumb is independent. The modulus of elasticity thereof is 0.12 kg/cm at 20% elongation percentage, 0.26 kg/cm at 50%, and 0.4 kg/cm at 100%, respectively. The reference numeral 54 is a reinforcing member formed by laminating a interlining and a surface member. As the interlining, a urethane film having 100 micron thickness is used, wherein the modulus of elasticity is 0.26 kg/cm at 20% elongation percentage, 0.6 at 50%, and 0.9 kg/cm at 100%, respectively. As the surface member, a nylon tricot fabric stretchable in two directions having a weight per unit area of 120 g/m² and 30% elongation percentage is used. The modulus of elasticity of such reinforcing member is 0.30 kg/cm at 20% elongation percentage, at least 1.0 kg/cm at 50%, and at least 1.0 kg/cm at 100%, respectively. The reinforcing member 54 is unitarily formed so as to protect from the outside and covering from the thumb 55 to the thenar 56, the wrist 57, and a portion 58 of the forearm in the surface of the main body 51. The main body 51 is adhered with the reinforcing member 54 by doping a hot melt adhesive such as available under the tradename Quintac 3435 (made by Nippon Zeon Co., Ltd.) on the whole surface of the side of the reinforcing member.

According to the present invention, the reinforcing member having a pattern corresponding to the affected part is unitarily formed with the desired part of the tubular main body comprising an elastic material. Then, since the stress applied on the affected part by the main body changes in accordance with the movement of the affected part, it is possible to apply the appropriate force for fixing, supporting, and pressing on the needed part in accordance with the movements of the person who wears the supporter. Further, in case of a large movement by which the affected part gets into danger or is otherwise subject to injury, the stress for the affected part increases immediately by the action of the reinforcing member to inhibit large movement and to prevent the critical movement from occurring. Since the supporter is formed by the unitarily formed main body and the reinforcing member, the supporter does not need any conventional or complex auxiliary belt. The structure is very simple and the weight is very light. The attaching operation is very easy and there is no uncomfortable feeling while attaching or wearing the supporter. Furthermore, since it is a very simple structure, that is, the reinforcing member is cut to the desired pattern and is adhered to the surface of the main body, it is easy to manufacture, and it is possible to exchange with another pattern in accordance with the condition of the affected part, thereby realizing lower cost. By changing the surface ratio of the reinforcing member and the main body in the width direction, it is possible to make the force applied on the affected part an appropriate value also in the width direction.

Figure 7:
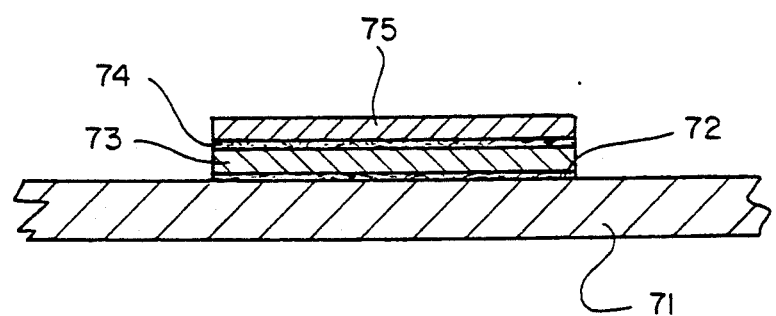
FIG. 7 is a fragmentary cross-sectional view of a portion of a typical supporter, showing the main body member and the layers of the reinforcing member thereof.

A typical cross-sectional view of a unitarily formed main body and reinforcing member according to the present invention and representative of the embodiments shown in FIGS. 1-5 is shown in FIG. 7. In FIG. 7, the numeral 71 denotes an elastic material forming the main body of the supporter; numeral 72 denotes an adhesive layer between the main body and the reinforcing member of the supporter; numeral 73 denotes an interlining layer of the reinforcing member having a greater modulus of elasticity than that of the main body 71; numeral 74 denotes another adhesive layer; and numeral 75 denotes a surface member for restricting the elongation of the interlining 72.

Thus there has been shown and described a novel construction in supporter which fulfills all of the objects and advantages set forth above. It will be apparent to those skilled in the art, however, that many changes, modifications, variations and other uses and applications for the subject invention are possible. All such changes, modifications, variations and other uses and applications which do not depart from the spirit and scope of the invention are deemed to be covered by the invention which is limited only by the claims which follow.

What is claimed is:

1. A supporter for mounting on an affected body part comprising a tubular main body member formed of an elastic material and a reinforcing member formed by laminating an interlining layer and a surface member, said interlining layer having a greater modulus of elasticity than that of said elastic material forming said main body member, said surface member having a greater modulus of elasticity than said interlining layer for restricting the elongation of said interlining layer, said reinforcement member being adhered only to a selected portion of said main body member, and said reinforcing member having a resultant modulus of elasticity greater than that of said main body member for restricting the elongation of said selected portion of said main body member to which said reinforcing member is adhered so as to be capable of restricting movement of the affected body part within a predetermined motion area.

2. A supporter for mounting on an affected body part comprising a tubular stretchable elastic material forming a main body having adhered to at least one selected portion of the main body a reinforcing member having a greater modulus of elasticity than said main body, said reinforcing member including an interlining layer laminated with a surface member which acts to restrict the elongation of said interlining layer, wherein said reinforcing member has a modulus of elasticity capable of restricting movement of the affected body part within a first motion area corresponding to a first predetermined range of elongation of said reinforcing member and capable of preventing movement of the affected body part within a second motion area corresponding to a second predetermined range of elongation of said reinforcing member greater than said first predetermined range of elongation.

3. A supporter in accordance with claim 2 wherein the affected body part is an anterior cruciate ligament and the supporter is a knee supporter.

4. The supporter in accordance with claim 2 wherein the affected body part is an unstable knee joint and the supporter is a knee supporter.

5. A supporter in accordance with claim 2 wherein the affected body part is an ankle and the supporter is an ankle supporter.

6. A supporter in accordance with claim 2 wherein the affected body part is a humerous outside epicondyle and the supporter is an elbow supporter.

7. A supporter in accordance with claim 2 wherein the affected body part is the tendon sheath in a wrist and the supporter is a hand and thumb supporter.

8. A supporter for mounting on a limb in position to cover a joint such as a knee joint, an ankle, an elbow or wrist and to predeterminedly constrain and limit movement thereof comprising a tubular member constructed of a fabric material characterized by being an elastic fabric adapted to fit snugly about said limb and joint and a pattern of a reinforcing material overlaying a predetermined defined area of the tubular member and characterized by being a laminated interlining and surface member having a higher modulus of elasticity than the elastic material of said tubular member and being attached thereto by a heat bonding adhesive agent, the predetermined defined area of the reinforcing material being selected to enable movements of the joint on which the tubular member is installed through a first predetermined motion area corresponding to the range of elongation of said tubular member, and said reinforcing material limiting movements of the joint through a second predetermined motion area greater than said first motion area and corresponding to the range of elongation of said reinforcing material, said reinforcing material substantially preventing movements of the joint through motions greater than said second predetermined motion area.

9. The supporter in accordance with claim 8 wherein said tubular elastic fabric is an elastic circular knitted fabric.

10. The supporter in accordance with claim 8 wherein said surface member of said reinforcing material is a nylon knitted tricot or raschel fabric.

11. The supporter in accordance with claim 8 wherein said interlining is a urethane non-woven or knitted fabric.

12. The supporter in accordance with claim 8 wherein the heat bonding adhesive is a liquid plastic adhesive activated by heat and adhered by pressure.

13. Support apparatus comprising an elastic body member having at least one tubular shaped portion for mounting on an affected body part, the elastic body member having an elasticity for maintaining said elastic body member in position on the affected body part, a reinforcing member adhered to a selected portion of the surface of the elastic body member, said reinforcing member having a shape defining a pattern corresponding to a predetermined portion of the affected body part and including a surface layer of a first material laminated to an interlining layer of a second material, said reinforcing member having an elasticity sufficient to enable movement of the corresponding predetermined portion of the affected body part through a first motion area corresponding to a predetermined limited range of motion, but limiting movement thereof through a motion area greater than said first motion area.

* * * * *